(12) United States Patent
Vert et al.

(10) Patent No.: US 6,350,812 B1
(45) Date of Patent: *Feb. 26, 2002

(54) HYDROGELS CONTAINING TRIBLOCK COPOLYMERS, AND PREPARATION AND USE THEREOF

(75) Inventors: Michel Vert; Suming Li, both of Castelnau-le-Lez (FR); Iliya Rashkov, Sofia (BG); José-Luis Espartero-Sanchez, Seville (ES)

(73) Assignee: Centre National de la Recherche Scientifique (CNRS), Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,357
(22) PCT Filed: Nov. 29, 1996
(86) PCT No.: PCT/FR96/01901
  § 371 Date: Sep. 2, 1998
  § 102(e) Date: Sep. 2, 1998
(87) PCT Pub. No.: WO97/19973
  PCT Pub. Date: Jun. 5, 1997

(30) Foreign Application Priority Data

Nov. 29, 1995  (FR) .............................................. 95 14144

(51) Int. Cl.[7] .......................... C08L 67/04; C08G 63/08; A61K 9/14; A61K 47/34
(52) U.S. Cl. ........................ 524/845; 524/916; 523/103; 424/439; 424/486; 424/501; 525/88; 528/354; 528/271; 528/361; 528/499; 528/501
(58) Field of Search ................................. 528/354, 271, 528/499, 501, 361; 524/916, 845; 525/88; 523/103; 424/486, 439, 501

(56) References Cited

U.S. PATENT DOCUMENTS

| 4,452,973 A | * | 6/1984 | Casey et al. ................. 528/354 |
| 4,526,938 A | * | 7/1985 | Churchill et al. ........... 525/415 |
| 4,826,945 A | * | 5/1989 | Cohn et al. .................... 604/19 |
| 4,882,168 A | * | 11/1989 | Casey et al. ................. 424/468 |
| 5,019,094 A | * | 5/1991 | Bezwada et al. ........... 606/230 |
| 5,612,052 A | * | 3/1997 | Shalaby ....................... 528/354 |

FOREIGN PATENT DOCUMENTS

| EP | 0 092 918 A | 11/1983 |
| WO | WO 90/03768 A | 4/1990 |

OTHER PUBLICATIONS

Patent Abstracts of Japan, vol. 011, No. 365, Nov. 27, 1987 & JP 62 135504 A, (Mitsui Toatsu Chem Inc.), Jun. 18, 1987.

* cited by examiner

Primary Examiner—Tae H. Yoon
(74) Attorney, Agent, or Firm—Nixon & Vanderhye P.C.

(57) ABSTRACT

A soft hydrogel containing a triblock copolymer and water is disclosed. The copolymer has formula (I): X-G-Y, wherein G is a non-hydroxylated hydrophilic linear polymer block containing p repetitive units, where p is a number from 10 to 150, each of X and Y is a polyester block containing m and n repetitive units, respectively, and the ratio (m+n)/p is high enough for said copolymer to be water-insoluble, said ratio (m+n)/p being selected in such a way that adding water to a solution of the copolymer in a water-miscible organic solvent leads to the formation of a soft hydrogel capable of retaining an amount of water at least as great as the weight of said copolymer. Said hydrogel is suitable for retaining and gradually releasing hydrophobic substance and/or hydrophilic macromolecules, including drugs.

42 Claims, No Drawings

HYDROGELS CONTAINING TRIBLOCK COPOLYMERS, AND PREPARATION AND USE THEREOF

The subject-matter of the invention is novel hydrogels based on triblock copolymer, their preparation and their application.

It is known that hydrogels are obtained conventionally with solid materials which swell in water by absorbing significant volumes of water. Hydrogels are generally composed of polymers which form, in water, a three-dimensional network capable of retaining in particular large molecules, such as proteins. Hydrogels can be prepared from crosslinked hydrophilic polymers.

Hydrogels have been recommended in particular as implantable pharmaceutical substrates which make possible the gradual release of drugs and in particular of macromolecules, such as proteins. Hydrogels are generally non-biodegradable and the drug is released by a diffusion phenomenon.

Provision has recently been made for the preparation of biodegradable hydrogels based on poly (hydroxyacid) -poly (ethylene glycol) -poly (hydroxyacid) triblock copolymers by using water-soluble copolymers, with acrylate endings, which are crosslinked in situ by photopolymerization of aqueous solutions of the polymer; see A. S. Sawhney et al., Macromolecules, 26, 581–587 (1993).

Document EP-A-0,092,918 describes rigid implants composed of non-crosslinked block copolymers comprising a polypeptide having a pharmacological activity. These implants gradually swell by absorbing water present in the living medium in which they are implanted.

A novel process has now been discovered which makes it possible, starting with certain triblock copolymers, to very rapidly obtain soft hydrogels containing a weight of water at least equal to the weight of triblock copolymer. These soft hydrogels can be easily deformed and can in particular pass through a hollow needle having an internal diameter of 2 mm and in particular through a hollow needle with an internal diameter of 1 mm.

Whereas hydrogels were mainly used until now for the trapping and the gradual release of hydrophilic macromolecules, the hydrogels of the present invention exhibit the distinguishing feature of being able to retain not only hydrophilic macromolecules but also hydrophobic substances.

The subject-matter of the invention is thus a hydrogel based on triblock copolymer and on water, characterized in that it is provided in the form of a soft hydrogel comprising an amount of water at least equal, by weight, to that of the copolymer and in that the said copolymer corresponds to the formula (I):

X-G-Y          (I)

in which G is a non-hydroxylated hydrophilic linear polymer block comprising p repeat units, p being a number which can vary from 10 to 150, X and Y each represent a polyester block respectively comprising m and n repeat units, the ratio (m+n)/p being sufficiently high for the said copolymer to be insoluble in water and the said ratio (m+n)/p being chosen such that the addition of water to a solution of the copolymer in a water-miscible organic solvent causes the formation of a soft hydrogel capable of retaining an amount of water at least equal to the weight of the said copolymer.

The invention also relates to a product obtained by lyophilization of a hydrogel as defined above. Such a lyophilisate is capable of rapidly absorbing a high proportion of water and of restoring a water-swollen soft hydrogel analogous to the hydrogel from which it was produced.

The ratios (m+n)/p which are suitable can be determined in each case by routine experiments, as will be specified hereinbelow. Generally, the suitable ratios (m+n)/p are numbers between 1 and 5 approximately.

In particular, the ratio (m+n)/p can be chosen so that the said gel is capable of retaining an amount of water at least equal to twice the weight of copolymer which it contains.

The number p can vary in particular from 10 to 120 and in particular from 15 to 100.

Of course, the blocks X and Y can be alike, that is to say composed of the same repeat units.

Study of copolymers analogous to those of formula (I) shows that, when the ratio (m+n)/p is sufficiently low, the copolymers are soluble in water. When the said ratio increases, the corresponding copolymers are only slightly soluble in water and give cloudy solutions, probably due to the formation of micelles. When the said ratio increases further, the polymers become insoluble in water: brought into contact with water, the polymers, in the form of powders, do not pass into solution and no longer give rise to the formation of micelles, for example after 24 hours of contact with water at room temperature, even if the copolymers can swell slightly on contact with water.

In accordance with the discovery which forms the basis of the invention, such water-insoluble copolymers can give hydrogels starting from their solution in a water-miscible organic solvent, according to the method indicated hereinabove. However, when the length of the hydrophobic links X and Y, for the same central block G, increases (in other words, when the ratio (m+n)/p increases) beyond a certain value, the hydrogels thus obtained contain increasingly low amounts of water. It is thus easy to determine experimentally, for each type of polymer of formula (I), the value of the ratio (m+n)/p beyond which the hydrogels are no longer capable of retaining a large mass of water: in fact, with such polymers in solution in the water-miscible organic solvent, the formation of a water-swollen hydrogel is not observed when water is added but rather the formation of a precipitate of the copolymer which occupies a lower volume than that of the starting organic solution.

The optimum length of the X and Y chains can thus be determined by simple routine experiments.

For example, in the case of poly(lactic acid)poly(ethylene oxide)-poly(lactic acid) copolymers, it is observed that, when the ratio (m+n)/p is less than approximately 0.2, the copolymers are soluble in water. When the said ratio is between 0.2 and 1 approximately, the copolymers are only slightly soluble in water and give cloudy solutions. When the said ratio is greater than approximately 1, the copolymers are insoluble in water. With the latter copolymers, it is possible to obtain, starting from an organic solution of the copolymer, hydrogels capable of retaining an appreciable amount of water, when the ratio (m+n)/p is between 1 and 5 and in particular between 1 and 4 approximately. Particularly satisfactory hydrogels are obtained in particular when this ratio varies within the range from 1.5 to 3 approximately. The numbers m and n are thus such that the ratio (m+n)/p is greater than 1 and lower than a maximum value beyond which the said copolymer is no longer able to form a hydrogel capable, under the conditions indicated hereinabove, of retaining a weight of water at least equal to the weight of the said copolymer.

Other points of information on this subject will be given hereinbelow by describing the preparation of the hydrogels.

The polymer blocks which represent X and Y, in the formula (I), are hydrophobic linear polyester blocks. These are in particular aliphatic polyesters.

It is known that aliphatic polyesters can be obtained:
a) either by polycondensation of a hydroxyacid with itself or by polycondensation of several hydroxyacids,
b) or by polymerization by ring opening of lactones,
c) or by polycondensation of diacids and diols.

Among the polyesters derived from hydroxyacids, mention may in particular be made of those which derive from monomers chosen from lactic acid, glycolic acid, malic acid monoesters (for example, alkyl or aralkyl monoesters, or monoesters resulting from the monoesterification of malic acid with a hydroxylated active principle, in particular a hydrophobic active principle; see, for example, U.S. Pat. Nos. 4,320,753 and 4,265,247); lactides (D-lactide, L-lactide and D,L-lactide), glycolide, para-dioxanone, and the like. The polymer blocks represented by X and Y can also be copolymers formed by the said monomers with one another.

Among the polymers derived from diacids and diols, mention may be made, for example, of poly(ethylene glycol succinate).

The polymer block represented by G in the formula (I) is a hydrophilic polymer which can be chosen, for example, from the following: poly(ethylene glycol), polyvinylpyrrolidone, polyacrylamide, and the like.

The block copolymers of formula (I) are known or can be prepared in a known way.

The polymerization resulting in the formation of the X and Y links can be carried out in the presence of the preformed polymer G having suitably functionalized ends. For example, the production of block copolymers based on poly(hydroxyacid)s and on poly(ethylene glycol) has already been described; see in particular P. Cerrai et al., Journal of Materials Science: Materials in Medicine, 5 (1994), 308–313 and Patent Application EP-295,055. The starting materials are, on the one hand, lactide and, on the other hand, poly(ethylene glycol). The operation is preferably carried out by bulk polymerization in the presence of a catalyst which can be a metal, an organometallic compound or a Lewis acid. Mention may be made, among the catalysts used, of zinc powder, calcium hydride, sodium hydride, tin octanoate, and the like. The length of the poly(hydroxyacid) chains depends essentially on the molar ratio (lactic units)/(PEG) in the initial mixture. The length of the poly(hydroxyacid) chains also increases with the duration of the reaction, which can range, for example, from a few minutes to a few days.

By using polymer blocks of type G with functionalized ends, for example carrying hydroxyl, carboxylic acid, amino or thiol terminal groups and the like, it is possible to obtain block copolymers, corresponding to the formula (I) hereinabove, in which the junction between X and G and between Y and G is made via an ester, amide, urethane or thioester group, and the like.

The copolymers of formula (I) can also be prepared from preformed polymer blocks by using a polymer of type G, the two ends of which are, in a known way, suitably functionalized, and polymers of type X and Y having a single functionalized end, so as to be able to react with a functionalized end G, with formation of a covalent bond.

The hydrogels of the invention form a three-dimensional network of hydrophilic chains (G) connected via hydrophobic microdomains composed, by aggregation, of poly(hydroxyacid) links (X and Y). This results in a physical crosslinking of the hydrophilic chains. The hydrophobic microdomains formed by the aggregates of links X and Y are analogous to nanoparticles which exhibit the distinguishing feature of not being free and independent because they form part of the three-dimensional network formed by the copolymer in the hydrogel. These kinds of nanoparticles are capable of dissolving and thus of retaining hydrophobic substances, for example medicaments.

The hydrogels of the invention can also retain, in their three-dimensional network, water-soluble macromolecules, such as proteins, which can be, for example, medicaments.

For example, other proteins (in particular immunoglobulins) and protein-antigen conjugates, the protein of which was tetanus anatoxin and the antigens of which were either polyglycosides or polyglycoside fragments from *Streptococcus pneumoniae* or polyglycosides or polyglycoside fragments from *Salmonella typhi*, have been incorporated in hydrogels according to the invention.

The hydrogels of the invention are evolving gels which are gradually degraded by hydrolysis reactions which randomly split ester groups of the X and Y blocks. The hydrolysis products of the X and Y blocks initially remain incorporated in the hydrophobic aggregates formed during the preparation of the hydrogel. When the hydrogel is in contact with an aqueous medium, this hydrolysis leads to the gradual release, by solubilization in aqueous medium, of polymers formed of G links optionally bonded to sufficiently short poly(hydroxyacid) blocks, such polymers being soluble in water. This results in a gradual disintegration of the hydrogel, which takes place on contact with the aqueous medium and which can be accompanied by the release into the said medium of a portion of the hydrophilic macromolecules, of the short fragments originating from the degradation of X and Y and of the hydrophobic substances possibly also present in the hydrogel.

The invention also relates to a process for the preparation of a hydrogel as defined above. This process is mainly characterized in that a solution of a copolymer X-G-Y as defined above in a water-miscible organic solvent is prepared and then this solution is brought into contact with a sufficient amount of water to form a soft hydrogel. This soft hydrogel is swollen with liquid (organic solvent and water). In order to remove the organic solvent, the hydrogel can subsequently be washed with water and/or subjected to dialysis against water and/or lyophilized.

It is possible, in order to bring the organic solution into contact with water, either to pour the organic solution into water or to pour water into the organic solution.

The following procedure can in particular be used to prepare the hydrogels of the invention: the copolymer is dissolved in a water-miscible organic solvent and then water is subsequently added, so as to obtain the formation of a soft gel.

Water can be added all at once or gradually but, however, not excessively slowly, in order to avoid a hydrogel being obtained which is dispersed and lacking in cohesion. In fact, the rate of addition of the water (or the rate of addition of the organic solvent to water when this other method is chosen) which is suitable in each case can be determined beforehand by simple routine experiments.

The water-miscible solvent must be a good solvent for both types of blocks, X and Y on the one hand and G on the other hand. Use may be made, among usable solvents, of acetone, dioxane, tetrahydrofuran, dimethylformamide or dimethyl sulphoxide.

The organic solvent which is present, as well as the water, in the hydrogel obtained can be removed by repeated washing operations with water or by dialysis. Lyophilization makes it possible to remove both the organic solvent and the water.

The hydrogels of the invention are in particular those which are prepared by the process which has just been shown.

In order to incorporate a hydrophilic macromolecule in a hydrogel according to the invention, the water can be replaced, in the process which has just been described, by an aqueous solution of the said macromolecule.

Likewise, in order to incorporate a hydrophobic substance in the hydrogels of the invention, the water-soluble organic solvent can be replaced, in the process which has just been described, by a solution of the hydrophobic substance in the said organic solvent.

It is possible, in order to select the copolymers capable of giving hydrogels retaining a sufficient proportion of water, to operate, for example, in the following way: 200 mg of the copolymer are dissolved in a volume, which can range from 0.4 to 0.8 cm$^3$, of one of the organic solvents indicated, for example acetone. 4 cm$^3$ of water are gradually added, so as to form a hydrogel. The hydrogels which, after removal of the excess liquid, have a mass at least equal to 0.4 g are, for example, selected.

The hydrogels of the invention can gradually release, in particular under the effect of the degradation of the X and Y links (as indicated hereinabove), the hydrophobic substances which are dissolved therein.

Moreover, the hydrogels of the invention exhibit the distinguishing feature of being biodegradable and bioresorbable. Degradation studies on these triblock copolymers have shown that the polyester chains are gradually degraded by hydrolysis, the final products being the corresponding hydroxyacids (or diacids and diols), which are bioresorbable.

This hydrolysis of the polyester chains, when it is continued, finally releases the hydrophilic polymer G forming the central block of the triblock copolymer. It is known that such polymers of relatively low molecular mass (less than 10,000) are bioresorbable: they are removed by the kidneys.

The G polymers mentioned and the monomers constituting the X and Y chains of the triblock copolymers which form the hydrogels of the present application are non-toxic biodegradable or bioresorbable compounds which are well tolerated by the body.

The hydrogels can thus be used in particular as pharmaceutical compositions which make it possible in particular to gradually release the medicaments which they contain. Such compositions prove to be particularly advantageous in the case of active principles regarded as insoluble in water. The compositions of the invention can also be used to gradually release hydrophilic active principles and in particular hydrophilic macromolecules, as mentioned above.

Mention will in particular be made, among the hydrophobic substances which can be incorporated in the hydrogels of the invention, of: hormones, in particular steroidal hormones (for example, progesterone, oestradiol, norgestrel, norethisterone, testosterone, hydrocortisone, prednisolone or dexamethasone), other hormones (for example, prostaglandins, insulin, and the like), antibiotics or antiparasitics (for example, griseofulvin, erythromycin or quinazoline and its derivatives), anticancer agents (for example, nitrosoureas, fluorouracil, azathioprine, doxorubicin, bleomycin, cisplatin or mitomycin), anaesthetics or sedatives (for example, tetracaine, chlorpromazine, diazepam, methadone or naltrexone), or other active principles, such as theophylline, caffeine or quinidine, or peptides (in particular vasopressin).

Immunogens (in particular proteins or protein-antigen conjugates, for example antigen-tetanus anatoxin conjugates, obtained in a way known per se) and optionally adjuvants can also be incorporated in the hydrogels of the invention. Such gels can be used as vaccinating agents which exhibit the advantage that, because of the gradual release of the immunogen, the body is in contact with the latter for a longer time.

The pharmaceutical compositions of the invention can be used in therapeutic treatment processes comprising their administration in particular by the oral or rectal route. The hydrogel of the corresponding lyophilisate can be encapsulated in a material capable of disintegrating by melting, softening or dissolution on contact with the body or body fluids. These compositions can also be administered in the form of soft implants, in particular by injection.

As indicated above, the hydrogels according to the invention are soft products, which can have a distinctive shape but which can then easily be deformed, for example under the pressure of a finger, like the well known hydrogels formed by gelatin or tapioca. The hydrogels of the invention and the compositions containing them are in particular hydrogels which are sufficiently deformable to be able to pass through a hollow needle having, for example, an internal diameter of 2 mm or even 1 mm.

The hydrogels of the invention can also be used as implantable and bioresorbable substrate intended to promote the regeneration of the periodontium according to the guided tissue regeneration technique (for example, instead of the membranes described in the document The hydrogels can be sterilized, in particular by UV irradiation, but it is generally preferable to prepare them under sterile conditions.

Colorants, aromatic substances, insecticides, and the like can also be incorporated in the hydrogels of the invention.

The hydrogels of the invention can be used in particular as substrates for the sustained diffusion of fragrances, flavours or insecticides.

It is also possible to incorporate, in the hydrogels of the invention, one or more hydrophobic substances which serve to modulate the stability of the aggregates forming the hydrophobic microdomains. It is possible, for example, to add oligomers obtained from the same monomers as those constituting the X and Y blocks of the formula (I).

Another subject-matter of the invention is a process for trapping a hydrophobic substance in a hydrogel, characterized in that a solution of a hydrophobic substance and of a triblock polymer, such as defined above, is prepared in a water-miscible organic solvent which is a solvent for the said hydrophobic substance and for the copolymer and then the said solution is brought into contact with water, in order to obtain a hydrogel which is capable of retaining the said hydrophobic substance. The operation can be carried out as already described above. The organic solvent is chosen from those mentioned hereinabove.

The invention also relates to a process for trapping a hydrophilic macromolecule in a hydrogel, characterized in that a solution comprising a triblock copolymer as defined hereinabove is prepared in a water-miscible organic solvent and in that the said solution is then brought into contact with an aqueous solution of the said macromolecule, in order to obtain a hydrogel capable of retaining the said macromolecule. The operation can be carried out as already described above.

The invention of course applies to the hydrogels, such as defined hereinabove, in which at least one hydrophobic substance and/or one hydrophilic macromolecule is dissolved.

The rate of degradation of the copolymers forming the hydrogels of the invention depends in part on the more or less amorphous or crystalline nature of the X and Y links. It is known that it is possible to partly control the amorphous or crystalline nature of such links. For example, the production of X and Y links starting from racemic lactide (instead of an enantiomer) promotes the production of amorphous links; furthermore, it is known that the crystallinity of the X and Y links increases with the length of these links; see in particular P. Cerrai et al., article cited hereinabove. The rate of degradation can thus consequently be adjusted.

The following examples illustrate the invention.

EXAMPLES

Example 1

Preparation of Copolymers 1.1. 0.4 mol of D,L-lactide (source: Purac, Netherlands) is mixed, in a round-bottomed flask, with 0.4 mol (as oxyethylene repeat units) of PEG 2000 (Fluka, Switzerland) and 37.6 mg (0.05% of the total weight of the reactants) of zinc powder (Merck, Germany). The PEG 2000 was purified beforehand by dissolving in chloroform and precipitating from diethyl ether at −10° C.

It will be recalled that the lactide molecule comprises 2 mol of lactate. The ratio of the number of lactate units to the number of oxyethylene units in the starting mixture is thus equal to two.

After degassing the reaction mixture under vacuum, it is heated at 140° C. under an argon atmosphere until the mixture is entirely in liquid form. A vacuum of $10^{-2}$ mm of mercury is subsequently produced, the round-bottomed flask is sealed and it is placed in an oven at 140° C. for 7 days. The round-bottomed flask is subsequently brought back to room temperature and its contents are dissolved in acetone and then subjected to precipitation from ethanol.

The product obtained is subsequently dried under reduced pressure.

The copolymer is analysed by $^1$H NMR. It was determined, from the ratio of the integral of the C$\underline{H}$ protons of the PLA blocks at 5.3–5.1 ppm to the integral of the (O—C$\underline{H}_2$—C$\underline{H}_2$) protons of the PEO block at 3.5 ppm, that the LA/EO molar ratio in the copolymer is equal to 2.1. It is deduced therefrom that the molecular mass of the copolymer is approximately 8800.

1.2. In a way analogous to that described in Example 1.1, a copolymer was prepared, starting from PEG 2000 and D,L-lactide (1.5 mol per 1 mol (as oxyethylene repeat units) of PEG) and from zinc powder (0.05% of the total weight of the reactants), characterized by $^1$H NMR by an LA/EO molar ratio equal to 2.3, giving a molecular mass of approximately 9400.

1.3. In an analogous way, starting from a mixture of 1.5 mol of D,L-lactide and of 1 mol (as oxyethylene repeat units) of PEG 2000, in the presence of calcium hydride (Janssen, Belgium) in the proportion of two mol of hydride per mole of PEG, a copolymer is obtained characterized by an LA/EO ratio equal to 3.2, giving a molar mass of approximately 12,300.

1.4. In a way analogous to that described in Example 1.3, a copolymer was prepared, starting from an equimolar mixture of lactide and PEG 2000 in the presence of calcium hydride, having a molecular mass of approximately 8000.

The equimolar mixture mentioned above refers, for the PEG, to moles of oxyethylene repeat units.

1.5. In a way analogous to that described in Example 1.1, a copolymer was prepared, starting from PEG 1000, D,L-lactide, in the proportion of one mole per 1 mol (as oxyethylene repeat units) of PEG, and zinc powder, characterized by $^1$H NMR by an LA/EO ratio equal to 3.4, giving a molar mass of approximately 6400.

Example 2

Production of Hydrogels 200 mg samples of copolymer are dissolved in 0.4 cm$^3$ of acetone (or in 0.8 cm$^3$ of acetone), and 4 cm$^3$ of water are gradually added. The copolymers used are those of Examples 1.1 to 1.5. In each case, a soft gel (hydrogel comprising a high proportion of water) is obtained.

By repeatedly removing the excess water and replacing it with a fresh amount of water, the acetone is removed.

It is also possible to remove the acetone by dialysis or by slow evaporation.

The water comprised in the hydrogel can be removed by lyophilization. The lyophilisate, placed in the presence of water, rapidly absorbs a weight of water at least equal to the weight of copolymer which it comprises and a water-swollen soft hydrogel is obtained.

Example 3

Incorporation of a Hydrophobic Substance in a Hydrogel 1 g of copolymer of Example 1.3 and 5 mg of commercial colorant Yellow OB are dissolved in 2 cm$^3$ of acetone.

This is a very hydrophobic, water-insoluble colorant. Distilled water (4 cm$^3$) is gradually added. A gel is obtained which occupies virtually all the volume of the starting acetone solution.

The gel is coloured homogeneously, without the appearance of colorant crystals.

On carrying out the procedure in an analogous way, but in the absence of copolymer, the colorant crystallizes during the addition of water.

On washing the gel with water, as described above, in order to remove the acetone, the colorant remains present in the gel.

Hydrogels in which progesterone is incorporated were prepared in an analogous way. Even after washing the gel several times with water, the greater part of the progesterone remains trapped in the gel. During the operations in which the gel is washed with water, there is no formation of a progesterone precipitate, in contrast to what is observed when water is added to a solution of progesterone in acetone. When administered by subcutaneous injection, the gel constitutes a bioresorbable soft implant which gradually releases the progesterone.

Example 4

Incorporation of a Protein

In a way analogous to that described above, 1 g of copolymer of Example 1.3 is dissolved in 2 cm$^3$ of acetone, and water containing 10 g/l of bovine albumin in solution is gradually added.

The gel obtained is washed 4 times with water.

A volume of physiological serum equal to the volume of the gel is added.

The excess liquid is examined for the protein (by UV analyses carried out every 2 minutes). The protein only becomes detectable after 6 minutes and the release extends over several hours).

In an analogous way, other proteins (in particular immunoglobulins) and protein-antigen conjugates, in which the protein was tetanus anatoxin and the antigens were either polyglycosides or polyglycoside fragments from Streptococcus pneumoniae or polyglycosides or polyglycoside fragments from Salmonella typhi, were incorporated in hydrogels according to the invention.

What is claimed is:

1. A process for preparing a hydrogel based on triblock copolymer and on water, provided in the form of a soft hydrogel comprising an amount of water at least equal, by weight, to that of the said triblock copolymer wherein said copolymer corresponds to the formula (I):

X-G-Y (I)

in which G is a non-hydroxylated hydrophilic linear polymer block comprising p repeat units, p being a number in the range of from 10 to 150, X and Y each represent a polyester block respectively comprising m and n repeat units, the ratio (m+n)/p being sufficiently high for the said copolymer to be insoluble in water and the said ratio (m+n)/p being chosen such that the addition of water to a solution of the copolymer in a water-miscible organic solvent causes the formation of a soft gel capable of retaining an amount of water at least equal to the weight of the said copolymer;

said process comprising preparing a copolymer X-G-Y in a water-miscible organic solvent and contacting said copolymer and solvent with a sufficient amount of water to form a soft hydrogel.

2. A process according to claim 1, wherein p is a number in the range of from 10 to 120.

3. A process according to claim 1, wherein the said ratio (m+n)/p is chosen so that the said gel can retain an amount of water at least equal to twice the weight of copolymer which it comprises.

4. A process according to claim 1, wherein the ratio (m+n)/p is a number between about 1 and 5.

5. A process according to claim 1 wherein X and Y represent a component selected from the group consisting of:

(i) polymers which derive from monomers chosen from the group consisting of lactic acid, glycolic acid, malic acid monoesters, lactides, glycolide and para-dioxanone, (ii) copolymers of monomers selected from the group consisting of lactic acid, glycolic acid, malic acid, monoesters, lactides, glycolide and paradioxanone and (iii) polymers obtained by polycondensation of di acids and diols.

6. A process according to claim 1 wherein the polymer block represented by G is chosen from the group consisting of poly(ethylene glycol), poly(vinylpyrrolidone) and polyacrylamide.

7. A process according to claim 1, wherein said hydrogel comprises a hydrophobic substance.

8. A process according to claim 7, wherein said hydrophobic substance is chosen from the group consisting of medicaments, colorants, aromatic substances and insecticides.

9. A process according to claim 7 wherein said hydrophobic substance is chosen from the group consisting of hormones, antibiotics, antiparasitics, anticancer agents, anesthetics, sedatives and peptides.

10. A process according to claim 1, said hydrogel comprises a water-soluble macromolecule.

11. A process of forming a lyophilisate of a hydrogel comprising lyophilizing a hydrogel formed from a process as defined in claim 1.

12. Process for the preparation of a hydrogel based on triblock copolymer and on water, provided in the form of a soft and deformable hydrogel comprising an amount of water at least equal, by weight, to twice that of the said triblock copolymer wherein the said copolymer corresponds to the formula (I):

X-G-Y (I)

in which G is a non-hydroxylated hydrophilic linear polymer block comprising p repeat units, p being a number in the range of from 15 to 150, X and Y each represent a polyester block respectively comprising m and n repeat units, X and Y represent a component selected from the group consisting of:

(i) polymers which derive from monomers chosen from the group consisting of lactic acid, glycolic acid, malic acid monoesters, lactides, glycolide and para-dioxanone, and (ii) copolymers of monomers selected from the group consisting of lactic acid, glycolic acid, malic acid monoesters, lactides, glycolide and para-dioxanone, the ratio (m+n)/p being sufficiently high for the said copolymer to be insoluble in water and the said ratio (m+n)/p being chosen such that the addition of water to a solution of the copolymer in a water-miscible organic solvent causes the formation of a soft and deformable hydrogel capable of retaining an amount of water at least equal to twice the weight of the said copolymer, said gel being sufficiently deformable to be able to pass through a hollow needle having an internal diameter of 2 mm, said process comprising preparing a copolymer X-G-Y in a water-miscible organic solvent and contacting said copolymer and solvent with a sufficient amount of water to form a soft hydrogel.

13. Process according to claim 12, further comprising washing said hydrogel with water and/or dialyzing said hydrogel and/or lyophilizing said hydrogel.

14. Process for the trapping of a hydrophobic substance in a hydrogel, comprising preparing a solution of a hydrophobic substance and of a triblock copolymer in a water-miscible organic solvent which is a solvent for said hydrophobic substance and for the copolymer and then contacting said solution with water, in order to obtain a soft hydrogel which is capable of retaining the said hydrophobic substance, said triblock copolymer corresponding to the formula (I):

X-G-Y (I)

in which G is a non-hydroxylated hydrophilic linear polymer block comprising p repeat units, p being a number in the range of from 10 to 150, X and Y each representing a polyester block respectively comprising m and n repeat units, the ratio (m+n)/p being sufficiently high for the said copolymer to be insoluble in water and the said ratio (m+n)/p being chosen such that the addition of water to a solution of the copolymer in a water-miscible organic solvent causes the formation of a soft gel capable of retaining an amount of water at least equal to the weight of the said copolymer.

15. Process for the trapping of a hydrophilic macromolecule in a hydrogel, wherein a solution comprising a triblock copolymer corresponding to the formula (I):

X-G-Y (I)

in which G is a non-hydroxylated hydrophilic linear polymer block comprising p repeat units, p being a number in the range of from 10 to 150, X and Y each representing a polyester block respectively comprising m and n repeat units, the ratio (m+n)/p being sufficiently high for the said copolymer to be insoluble in water and the said ratio (m+n)/p being chosen such that the addition of water to a solution of the copolymer in a water-miscible organic solvent causes the formation of a soft-gel capable of retaining an amount of water at least equal to the weight of the said copolymer, is prepared in a water-miscible organic solvent and then the said solution is brought into contact with an aqueous solution of the said macromolecule, in order to obtain a soft hydrogel capable of retaining the said macromolecule.

16. The process of claim 1 wherein p is a number in the range of 15 to 100.

17. A process of claim 14 wherein p is in the range of 15–150.

18. A process of claim 15 wherein p is in the range of 15–150.

19. A process of claim 14 wherein X and Y represent a component selected from the group consisting of:
(i) polymer, which derive from monomers chosen from the group consisting of lactic acid, glycolic acid, malic acid monoesters, lactides, glycolide and para-dioxanone, (ii) copolymers of monomers selected from the group consisting of lactic acid, glycolic acid, malic acid, monoesters, lactides, glycolide and paradioxanone and (iii) polymers obtained by polycondensation of diacids and diols.

20. A process of claim 15 wherein X and Y represent a component selected from the group consisting of:
(i) polymers which derive from monomers chosen from the group consisting of lactic acid, glycolic acid, malic acid monoesters, lactides, glycolide and para-dioxanone, (ii) copolymers of monomers selected from the group consisting of lactic acid, glycolic acid, malic acid, monoesters, lactides, glycolide and paradioxanone and (iii) polymers obtained by polycondensation of diacids and diols.

21. A process of claim 14 wherein the ratio (m+n)/p is chosen so that the said gel can retain an amount of water at least equal to twice the weight of copolymer which it comprises.

22. A process of claim 15 wherein the ratio (m+n)/p is chosen so that the said gel can retain an amount of water at least equal to twice the weight of copolymer which it comprises.

23. A process of claim 14 wherein said hydrophobic substance is chosen from the group consisting of medicaments, colorants, aromatic substances and insecticides.

24. A process of claim 12 wherein said ratio (m+n)/p is a number between 1 and 5 approximately.

25. A process of claim 14 wherein said ratio (m+n)/p is a number between 1 and 5 approximately.

26. A process of claim 15 wherein said ratio (m+n)/p is a number between 1 and 5 approximately.

27. A process according to claim 1 characterized in that, in addition, the said hydrogel is washed with water and/or subjected to dialysis against water and/or lyophilized.

28. A process according to claim 12 characterized in that the polymer block represented by G is chosen from the group consisting of poly(ethylene glycol), poly(vinylpyrrolidone) and polyacrylamide.

29. Hydrogel based on triblock copolymer and on water, characterized in that it is provided in the form of a soft and deformable hydrogel comprising an amount of water at least equal, by weight, to twice that of the said triblock copolymer and in that the said copolymer corresponds to the formula (I):

$$X\text{-}G\text{-}Y \qquad (I)$$

in which G is a non-hydroxylated hydrophilic linear polymer block comprising p repeat units, p being a number in the range of from 15 to 150, X and Y each represent a polyester block respectively comprising m and n repeat units, X and Y represent a component selected from the group consisting of:
(i) polymers which derive from monomers chosen from the group consisting of lactic acid, glycolic acid, malic acid monoesters, lactides, glycolide and para-dioxanone, and (ii) copolymers of monomers selected from the group consisting of lactic acid, glycolic acid, malic acid monoesters, lactides, glycolide and para-dioxanone, the ratio (m+n)/p being sufficiently high for the said copolymer to be insoluble in water and the said ratio (m+n)/p being chosen such that the addition of water to a solution of the copolymer in a water-miscible organic solvent causes the formation of a soft and deformable hydrogel capable of retaining an amount of water at least equal to twice the weight of the said copolymer, said gel being sufficiently deformable to be able to pass through a hollow needle having an internal diameter of 2 mm.

30. Hydrogel according to claim 29, characterized in that p is a number in the range of from 15 to 120.

31. Hydrogel according to claim 29, wherein said ratio (m+n)/p is a number between 1 and 5 approximately.

32. Hydrogel according to claim 29 wherein the polymer block represented by G is chosen from the group consisting of poly(ethylene glycol), poly(vinylpyrrolidone) and polyacrylamide.

33. Hydrogel according to claim 29, further comprising a hydrophobic substance.

34. Hydrogel according to claim 33, wherein said hydrophobic substance is chosen from the group consisting of medicaments, colorants, aromatic substances and insecticides.

35. Hydrogel according to claim 33 wherein said hydrophobic substance is chosen from the group consisting of hormones, antibiotics, antiparasitics, anticancer agents, anesthetics, sedatives and peptides.

36. Hydrogel according to claim 29, further comprising a water-soluble macromolecule.

37. A composition comprising, as substrate, a hydrogel as defined in claim 29.

38. A pharmaceutical composition comprising a hydrogel as defined in claim 29 and a pharmaceutically acceptable carrier.

39. Composition according to claim 38, further comprising a medicament comprising a water-soluble macromolecule.

40. Composition according to claim 38, which is sufficiently deformable to be able to pass through a hollow needle having an internal diameter of 1 mm.

41. A hydrogel produced by the process of claim 1.

42. A hydrogel produced by the process of claim 12.

* * * * *